United States Patent [19]
Weiss

[11] Patent Number: 5,025,785
[45] Date of Patent: Jun. 25, 1991

[54] DIABETES DETECTION METHOD

[76] Inventor: Jeffrey N. Weiss, 2202 Lucaya Bend, E-4, Coconut Creek, Fla. 33066

[21] Appl. No.: 418,109

[22] Filed: Oct. 6, 1989

Related U.S. Application Data

[63] Continuation-in-part of Ser. No. 672,717, Nov. 19, 1984, Pat. No. 4,895,159, which is a continuation-in-part of Ser. No. 416,654, Sep. 10, 1982, abandoned.

[51] Int. Cl.$^5$ .............................................. A61B 6/00
[52] U.S. Cl. ................................... 128/633; 128/898; 128/665
[58] Field of Search ................ 128/633, 634, 665, 898

[56] References Cited
U.S. PATENT DOCUMENTS
4,715,703 12/1987 Cornsweet et al. ................. 128/633

Primary Examiner—Max Hindenburg
Assistant Examiner—David Shay
Attorney, Agent, or Firm—Wolf, Greenfield & Sacks

[57] ABSTRACT

A noninvasive method for detecting the presence of diabetes mellitus and for monitoring physical changes caused by that disease is disclosed. In performing the method, a beam of light from a low powered laser is directed at a clear site in the lens of a patient's in vivo eye. The variations in intensity of the light back-scattered from the site are utilized to derive a measurement of the diffusion coefficient. Alternatively, or in addition to taking measurements from the lens, measurements may be taken from the conjunctiva, the cornea, or the retina of the vivo eye. It has been found that the diffusion coefficient decreases more rapidly versus age in persons having diabetes mellitus than in nondiabetic persons of comparable age. By relating the variations in intensity of back-scattered light with the patient's age and by comparison with corresponding measurements taken from nondiabetic persons of comparable age, the presence of diabetes mellitus can be determined. Measurement of the back-scattered light also permits the amount of damage caused by that disease and the efficacy of treatment to be assessed.

4 Claims, 2 Drawing Sheets

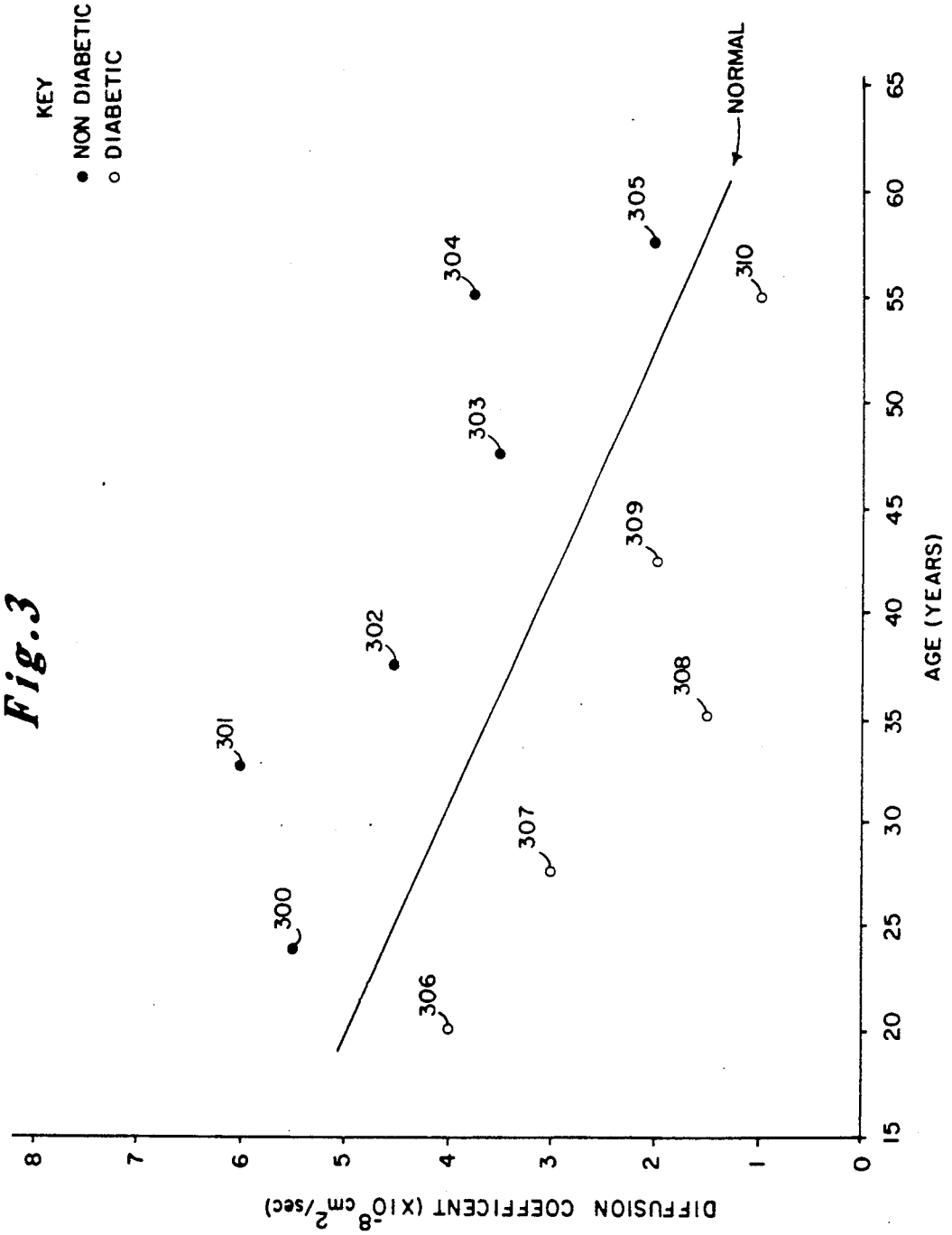

DIABETES DETECTION METHOD

CROSS-REFERENCE TO RELATED APPLICATIONS

This application is a continuation-in-part of my application Ser. No. 672,717, now U.S. Pat. No. 4,895,159, issued Jan. 23, 1990. That earlier application is a continuation-in-art of my parent patent application Ser. No. 416,654, which was filed on Sept. 10, 1982 and is now abandoned. Before that parent application was abandoned, a divisional patent application Ser. No. 671,520 was filed on Nov. 15, 1984 and became U.S. Pat. No. 4,883,351 issued on Nov. 28, 1989. Applicant incorporates by reference into this application all of the specifications and claims of said earlier application and U.S. Pat. Nos. , 4,895,159, 416,654 and 4,883,351.

FIELD OF THE INVENTION

This invention relates to medical diagnostic and monitoring methods and, in particular, to a method for detecting, diagnosing and monitoring diabetes mellitus.

BACKGROUND OF THE INVENTION

Diabetes mellitus is one of the leading causes of morbidity and mortality in the United States. Although the disease, once diagnosed, can be controlled, the diabetic patient faces many complications, some of them life threatening. For example, the average life expectancy of the diabetic patient is one-third less than that of the general population; blindness is twenty five times as common, renal disease is seventeen times more common, gangrene is five times as common and heart disease is twice as common in diabetics as compared to the nondiabetic.

In addition, the incidence of this disease appears to be increasing—between 1936 and 1978 there was a six fold increase in the prevalence of the disease.

It is believed by many researchers in the field that many complications suffered by diabetic patients can be minimized or avoided by early detection of the onset of the disease and proper long-term control of the patient's blood glucose.

Unfortunately, prior art detection and monitoring methods have been unable to either accurately detect the onset of the disease at an early stage or assess the degree of control on a long-term basis. Such prior art detection methods, other than interpretation of clinical symptoms, rely on blood sugar measurements which reflect the presence of the disease. Prior art monitoring methods involve either spot blood sugar measurements or more complicated blood tests which reflect blood glucose levels that existed in the patient's body at a time three to five weeks prior to the time of measurement. Both prior art measurement methods require bodily invasion and the results are difficult to interpret.

Accordingly, it is an objective of this invention to detect the onset of diabetes mellitus prior to the appearance of clinical symptoms.

It is another object of this invention to detect the development of diabetic eye disease.

It is still another object of this invention to assess the effectiveness of various methods of diabetic treatment.

It is yet another object of this invention to determine the relationship and degree of control required to prevent the occurrence of diabetic complications.

It is a further object of this invention to provide a method for objectively quantifying the effects of systemic disease, trauma, drugs, local inflammatory conditions of the eye, and aging.

SUMMARY OF THE INVENTION

The foregoing objects are achieved from the ascertainment of the diffusion coefficient of the lens of a patient's in vivo eye by directing a beam of light from a low-power laser at a clear site in the lens of the patient's eye and measuring the intensity of the hack-scattered light. A number of measurements are taken of the diffusion coefficient for patients known to be normal to establish a diffusion coefficient-age relationship. The ascertained lens diffusion coefficient of the patient is compared to the established relationship. Where a significant decrease of lens diffusion coefficient over the normal diffusion coefficient-age relationship is obtained, there is a likelihood that the patient is diabetic. The amount of decrease of lens diffusion coefficient over the normal established diffusion coefficient can be used as a measure of the severity of the disease or to monitor the progress and treatment of the disease.

In lieu of or in addition to making measurements from the lens of the patient's in vivo eye, measurements may be taken from the conjunctiva, the cornea, and the retina of the patient's eye. Those parts of the eye are appreciably affected by diabetes mellitus in addition to the lens of the eye. Because measurements taken from the lens have thus far provided the best results, the invention is here described with the taking of measurements only from the lens of the eye. From that description, the extension of the measurement technique to the conjunctiva, cornea, or retina is self-evident.

The optical apparatus used in the performance of the method preferably consists of a low-power laser and associated optics attached to a slit-lamp biomicroscope equipped with precision mechanical adjustments to focus the light beam on the patient's lens. A photomultiplier is used to detect the intensity of the back-scattered light and a correlator is used to process the output of the photomultiplier to provide a set of numbers that can be used to calculate the diffusion coefficient.

BRIEF DESCRIPTION OF THE DRAWINGS

FIG. 3 is a graph of lens diffusion coefficient versus patient age. The graph was developed from information obtained by using the apparatus described herein.

DETAILED DESCRIPTION OF THE METHOD

Figure 1:
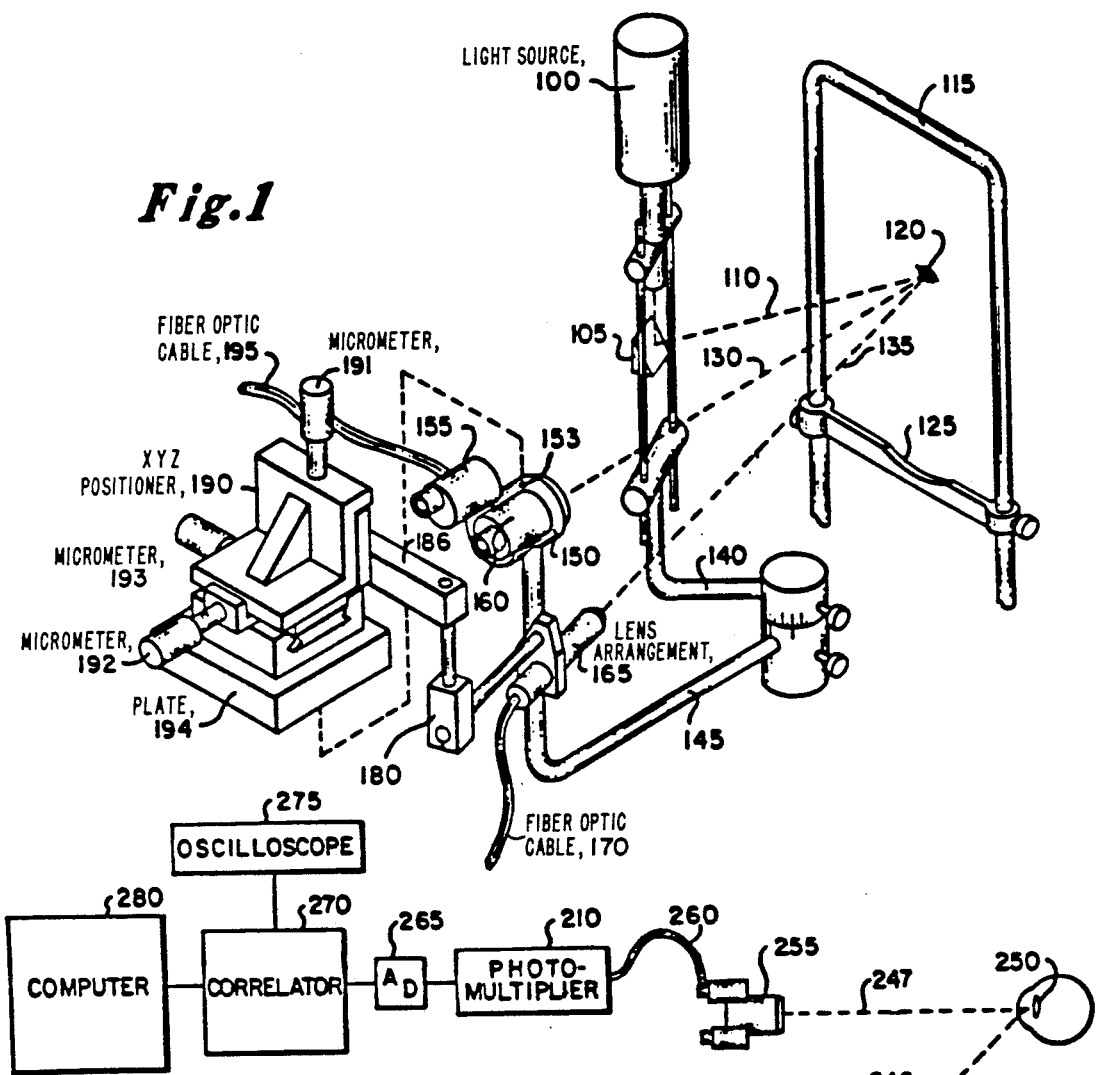
FIG. 1 is a perspective view of a slit-lamp biomicroscope and added equipment used to focus the light beam on the patient's lens.

FIG. 1 shows an optical arrangement for making measurements required in the performance of the method. That optical arrangement utilizes a modification of a commercially-available instrument known as a slit-lamp biomicroscope. This device is well known and is typically used in ophthalmological studies of the conjunctiva, cornea, lens and retina of the human eye. Slit-lamp biomicroscopes suitable for modification are manufactured by several companies and the operation and use of those devices are well known to ophthalmologists and others engaged in the examination of human eyes.

Basically, a slit-lamp biomicroscope consists of a light source, a microscope and a mechanical supporting arrangement that allows precise positioning of the light source and microscope relative to the patient to enable focusing of the light on selected portions of the patient's eye. Specifically, light produced by source 100 is reflected from mirror 105 and directed as beam 110 to the patient's eye shown schematically a eye 120. The apparatus also includes frame 115 and support 125 which position and hold the patient's head in a fixed position. Light which is reflected or scattered by the patient's conjunctiva, cornea, lens or retina, shown schematically as beam 130, is received by a binocular microscope arrangement 150 which has two eyepieces, 155 and 160. The lamp arrangement and microscope are supported by arms 140 and 145 from a common post, all in a well-known manner.

To facilitate making the requisite measurements, the standard slit-lamp biomicroscope is modified by the addition of an XYZ positioning apparatus to the microscope arrangement 150. In particular, the XYZ position apparatus consists of commercial XYZ positioner 190 which can obtain precise three-dimensional movement which is controlled by three orthogonal micrometers, 191-193. Positioner 190 is mounted on plate 194 which is in turn fastened to microscope arrangement 150 by means of a threaded hole 153 which is normally found on the arrangement and used for other purposes.

Attached to the movable surface of XYZ positioner 190 are arms 180 and 186 which support a lens arrangement 165. As will be hereinafter further explained, lens arrangement 165 is connected via fiber optic cable 170 to a laser and used to illuminate the patient's lens via beam 135. The back-scattered light shown schematically as beam 130 is detected by a sensor located in the focal plane of eyepiece 155 and conveyed via cable 195 to a photomultiplier (not shown).

Figure 2:
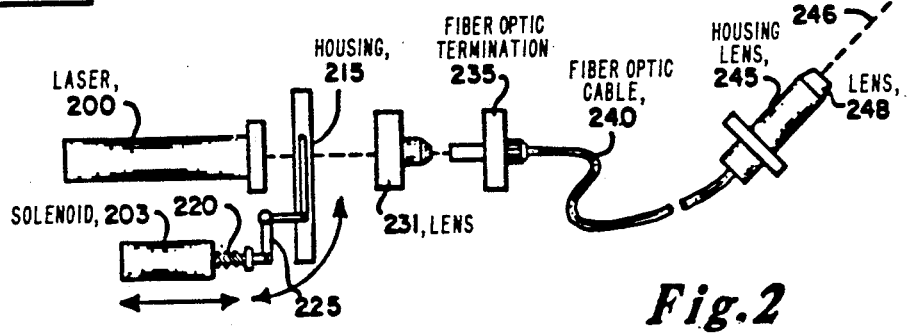
FIG. 2 shows an overall schematic view of the optical arrangement to irradiate the patient's lens and the apparatus used to process the resulting signal.

FIG. 2 of the drawings shows a schematic diagram of the preferred optical arrangement for making the measurements necessary to the performance of the method. The apparatus consists of a light source for illuminating a clear site in the lens of a patient's in vivo eye and a detecting or receiving portion for receiving the back scattered radiation.

The light source part of the apparatus consists of laser 200, two filters mounted in housing 215, microscope objective lens 231, fiber optic termination 235, fiber optic cable 240 and focusing lens arrangement 245. Laser 200 is a 5 milliwatt helium-neon laser of conventional design which is commercially available from several companies. A laser suitable for use with the illustrative embodiment is a model U-1305P, available from the Newport Corporation, 18235 Mount Baldy Circle, Fountain Valley, California. The output of laser 200 passes through two neutral density filters, mounted in housing 215. One filter is permanently mounted in the laser beam path and reduced the power output of laser 200 to 1.5 milliwatts. The other filter is solenoid-controlled so that it can automatically be moved out of the laser beam path during the measurement operation. When both filters are in place, they reduce the laser output power to 0.50 milliwatts. The movable filter is used during premeasurement focusing, as will hereinafter be described, in order to reduce the patient s exposure to unnecessary laser irradiation. The movable filter is controlled by solenoid 203 which is under control of a footswitch operated by the person making the measurement. When solenoid 203 is operated, arm 220 retracts, in turn, sliding the movable filter in housing 215 by means of bell crank 225.

After passing through one or both filters the attenuated laser output light enters lens 231. Lens 231 is a 40 x microscope objective lens which is mounted so that it focuses the laser light on the end of the optical fiber which transmits the light to the irradiating apparatus. Light passing through lens 231 falls onto an optical fiber 240 mounted in termination 235. The end of fiber 240 which enters termination 235 is attached to an XYZ positioner. The positioner is used to align the end of the optical fiber with the focusing lens to obtain maximum light transmission.

The other end of optical fiber 240 is attached to focusing lens arrangement 245. Lens arrangement 245 consists of a fiber optic holder which is slidably mounted in a lens holder tube. Lens 248 is an 18 mm focal-length converging lens which is mounted at the other end of the lens holder tube. The movable arrangement between the fiber optic holder and the lens allows small adjustments to be made between the end of the optical fiber and the lens to permit fine focusing of the laser output beam at a given position within the patient's lens. Lens arrangement 245 is connected to the XYZ positioner attached to the slit-lamp biomicroscope as previously described and is used to focus the laser beam, 246, such that a sharp focus is achieved at a clear site in the patient's lens 250. After passing through the focal point in the lens the beam becomes sharply defocused in order to maintain a low radiation level at the retina and prevent any possibility of injury or damage.

The detection optical system uses portions of the optical system of the slit-lamp biomicroscope. In particular, light back-scattered from the clear site in the patient s lens (represented schematically as beam 247) is focused by one objective of the binocular portion of microscope 255 onto a commercially-available optical fiber light guide, 260, located at the center of the focal point of the eyepiece. In the illustrated embodiment, the end termination of optical fiber light guide 260 replaces the normal left ocular of slit-lamp biomicroscope 255. The arrangement is such that the end of fiber cable 260 can be seen when looking through the left ocular to allow focusing of the back-scattered radiation on the end of the fiber cable.

Scattered light received at microscope 255 is fed by fiber optic guide 260 to photomultiplier 210 which is a well-known, commercially-available device. A photomultiplier suitable for use with the illustrative embodiment is a model number 9863B/350 manufactured by EMI Gencom, Inc., 80 Express Street, plainview, New York. The output of photomultiplier 210 is provided to amplifier-discriminator 265 which also is a well-known device that amplifies the output pulse signals produced by the photomultiplier and selectively sends to correlator 270 only those signals which have an amplitude above a preset threshold. A suitable amplifier-discriminator for use with the illustrated embodiment is a model number AD6 manufactured by Pacific Photometric Instruments Inc., 5675 Landregan Street. Emeryville, California.

The output of amplifier-discriminator 265 is, in turn, provided to a commercial photon correlation spectrometer 270 (a suitable spectrometer is a model DC64 manufactured by Langley-Ford Instruments, 85 North Whitney Street, Amherst, Massachusetts). Correlator 270 counts the number of pulses received from amplifier-discriminator 265 for a predetermined time interval and performs a well-known mathematical operation to obtain the correlation function. A suitable time interval is ten microseconds. The sample time may be chosen to further characterize the population of light scatterers. Measurements taken at shorter sample times, i.e., at 1.5 microseconds, appear to be more characteristic of smaller and/or faster scattering elements whereas measurements made at longer sample times, i.e. 200 microseconds, appear more characteristic of larger and/or slower scattering elements.

The correlator utilizes the received counts to solve the following equation for the autocorrelation function $C_m(t)$:

$$C_m(t) = \sum_{i=1}^{i=n} p_i p_i + m$$

where
t = the length of the predetermined time interval
i = an index number whose range is one to the total number of intervals
Pi = the number of pulses occurring during the ith time interval
n = the total number of intervals
m = an integer whose range is one to sixty-four.
In accordance with the above equation correlator 270 produces 64 solutions or points (one for each value of m) in a time sequence, each measurement separated by the value of t. These measurements may be plotted against time to produce a curve which may then be displayed for examination on oscilloscope 275. The values of the solutions may also be provided to computer 280 for further processing to determine the diffusion coefficient. A computer suitable for use with the illustrative embodiment is a personal computer manufactured by the International Business Machines Corporation. Armonk, New York.

In particular, the diffusion coefficient (D) is also related to the correlation function $C_m(t)$ determined by the correlator by the following equation:

$$C_m(t) = A + B\,e^{-2DK^2 m(t)}$$

where
A, B = Constants dependent on the physical details of the measurement
K = the scattering constant for the eye which is $4\pi/\lambda$ (sin $\theta/2$) where $\lambda$ is the wavelength and $\theta$ is the scattering angle
t = the length of the predetermined time interval
m = an integer whose range is one to sixty four.
Therefore, the values of the diffusion coefficient D and the constants A and B in the above equation can be determined, with the aid of computer 280, from the autocorrelation curve produced by the correlator 270 by using standard curve fitting and analysis techniques. The calculated diffusion coefficient can be stored in the computer along with other patient data, including, in accordance with the invention, the patient's age.

The apparatus shown in FIGS. 1 and 2 is used to perform a measurement of the lens diffusion coefficient as follows: with a patient sitting at the slit-lamp biomicroscope, the operator sets up the device in the same way that the device would be set up during a normal ophthalmic evaluation. In order to measure various positions within the periphery of the patient's lens it is necessary that the pupil be dilated using routinely-available dilating drops as normally used during the course of complete ophthalmic evaluation. Both the light produced by lamp 100 and the laser light with both filters in place are used to align the laser output as seen through the ocular 155 and 160 with the end of optical fiber light guide 195 in left ocular 155. Due to the standard adjustments on the biomicroscope and XYZ positioner 190, this alignment may be achieved at any selected site within the patient's lens. The operator selects a site that is clear, i.e. a site that is free of opacities.

Lamp 100 is then turned off and the operator depresses a foot switch which operates solenoid 203 sliding the movable filter in housing 215 out of the way to allow the actual measurement to be made using 1.5 milliwatts laser light power. A second foot switch adjacent to the first can be used to turn laser 200 off should any emergency arise.

The back-scattered light output is measured by the photomultiplier through the optical system previously described and the photomultiplier output is processed as previously described by the photon correlation spectrometer. While measurements are in progress, the output of the spectrometer may be monitored by the oscilloscope connected to it. A measurement is made, for example, for 5 seconds at which point the first foot switch is released, reinserting the movable filter into the optical path, and concluding the measurement.

When performing the method to screen for diabetes mellitus, measurements are taken only from "clear" sites in the lens of the eye. That is, measurements are taken only from sites in the lens that are non opaque. The yellowing of the lens that is normal in the human aging process is deemed not to be an opacity. In normal humans, discernable yellowing of the lens first appears at about 30 years of age and thereafter that yellowing tends to increase with age. Measurements taken from cataracts (i.e. from opacities in the lens) are deemed, at this time, to be unreliable because sufficient information has not yet been developed from clinical studies to enable such measurements to be linked with any certainty to diabetes mellitus.

In order to accurately compare measurements made from an individual with measurements made from the same individual at a later time or with measurements from a different individual, the compared measurements should be made from approximately the same position in the lens. Measurements obtained from other positions in the lens may give somewhat different results which can provide additional information concerning the health of the patient. For standardization purposes, it has been my practice to take measurements from a non-opaque site in the central nucleus of the lens.

By using the apparatus described herein, no contact lens, nor anesthetic drops are necessary to make a measurement. Although commonly used in eye examinations, anesthetic drops have various deleterious side effects. Such side effects include stinging, burning and conjunctival redness as well as severe allergic reactions with resulting central nervous system stimulation or corneal damage. In addition, application of a contact lens following the use of a topical anesthetic requires much patient cooperation as well as experience on the part of the examiner. Further complications arising from the use of a contact lens include corneal abrasions and infection as well as recurrent and chronic corneal erosions. In contrast, by employing the described apparatus, the method can truly be "non-invasive."

In using the method to detect and monitor diabetes, a calculation of the diffusion coefficient is made on a series of patients whose health is known and are believed to be nondiabetic. The resulting measurements are compared to the patient's age resulting in a curve or graph similar to that shown in FIG. 3 (hypothetical measurements are shown for illustrative purposes). FIG. 3 shows the value of the diffusion coefficient increasing in an upward direction along the vertical axis and patient age increasing rightward in the horizontal direction.

It has been discovered that the diffusion coefficient for patients who do not have diabetes (represented for example by points 300-305) all lie above a line (marked "normal" on the graph) while the diffusion coefficient for patients having diabetes lie below the line (represented by points 306-310). In addition, the severity of the disease is directly related to the distance below the line at which the ascertained diffusion coefficient lies, with increasing distance indicating greater severity. For example, the patient represented by point 308 usually exhibits more severe symptoms than the patient represented by point 310.

When a curve such as that shown in FIG. 3 has been established, patients can be screened for diabetes by comparing their ascertained diffusion coefficients with the "normal" line If the measurement is significantly below the "normal" line as shown in FIG. 3 the patient is likely to have diabetes or a disease which affects the lens similarly. Known diabetic patients can be monitored by making repeated measurements over a fixed period of time. The series of measurements are compared to the graph. An increasing distance from the "normal" line indicates an acceleration in the disease. A fixed distance indicates the disease appears to be under reasonable control.

I have found that measurements of back-scattered light may be taken from the conjunctiva, the cornea, and the retina of the eye. Those parts of the eye are appreciably affected by the presence of diabetes mellitus in addition to the lens of the eye. Thus far, however, measurements taken from the lens have given the best results. When measurements are taken from the cornea, it is important for comparison purposes, to take the measurements from the same layer of the cornea. The layers of the cornea (the epithelium, for example) are thin and care must be exercised to assure that the measurements are taken from the desired layer. Consequently, depth perception, when setting up and taking the measurements, is a requirement that must be strictly observed. For comparison purposes, it is preferred to take the measurements from approximately the same site in the layer. In this respect, however, that requirement is not as critical as when measurements are made from the lens. That is, considerable variation in the sites from which measurements are taken is permissible when measurements are taken from the cornea.

Where measurements are taken from the conjunctiva or from the retina, it is preferable to take the measurements from the surface at the front of conjunctiva or retina. Depth perception is important to assure that the measurements are taken from the front surface of the retina or conjunctiva. To prevent damage to the retina, low intensity light should be used. As with the cornea, it is not as critical, for comparison purposes, to take the measurements from the same site on the retina, cornea or the conjunctiva as it is when measurements are taken from the lens.

Changes and modifications within the spirit and scope of the invention will be apparent to those skilled in ophthalmology. As an example, the diffusion coefficient can be replaced by an equivalent measure such as the decay constant. The essential point is that variations in the intensity of the back-scattered light are the basis of the measurement. That measurement may then be utilized to obtain derivatives. The form in which those variations are presented is mainly a matter of individual preference. Such obvious modifications and changes are intended to be covered by the appended claims.

What is claimed is:

1. A noninvasive method of examining a patient for diabetes mellitus, comprising the steps of:
    A. ascertaining the variations in the intensity of light back-scattered from the cornea of an in vivo eye of each of a plurality of normal persons and deriving measurements therefrom,
    B. relating the derived measurements with the respective ages of the normal persons to obtain norms for persons of various ages,
    C. ascertaining the variations in the intensity of the light back-scattered from the cornea a corresponding measurement therefrom, and
    D. comparing the patient's measurement with the norm for persons of comparable age to the patient.

2. The method according to claim 1, wherein the measurements are made from the same layer of the cornea of the in vivo eyes of the patient and the normal persons.

3. A noninvasive method of examining a patient for diabetes mellitus, comprising the steps of:
    A. ascertaining the variations in the intensity of light back-scattered from the conjunctiva of the in vivo eye of each of a plurality of normal persons and deriving measurements therefrom,
    B. relating the derived measurements with the respective ages of the normal persons to obtain norms for persons of various ages,
    C. ascertaining the variations in the intensity of light back-scattered from the conjunctiva of the patient's in vivo eye and deriving corresponding measurements therefrom, and
    D. comparing the patient's measurements with the norm for persons of comparable age to the patient.

4. A noninvasive method of examining a patient for diabetes mellitus, comprising the steps of:
    A. ascertaining the variations in the intensity of light back-scattered from the retina of the in vivo eye of each of a plurality of normal persons and deriving measurements therefrom,
    B. relating the derived measurements with the respective ages of the normal persons to obtain norms for persons of various ages,
    C. ascertaining the variations in the intensity of light back-scattered from the retina of the patient's in vivo eye and deriving corresponding measurements therefrom, and
    D. comparing the patient's measurements with the norm for persons of comparable age to the patient.

* * * * *